(12) United States Patent
Saunders et al.

(10) Patent No.: US 12,672,966 B1
(45) Date of Patent: Jul. 7, 2026

(54) SUBCHONDRAL IMPLANT SYSTEM

(71) Applicants: James S. Saunders, San Antonio, TX
(US); Thomas Zink, San Antonio, TX
(US); Christopher Hyer, Columbus,
OH (US); Thomas Roukis, Winter
Garden, FL (US)

(72) Inventors: James S. Saunders, San Antonio, TX
(US); Thomas Zink, San Antonio, TX
(US); Christopher Hyer, Columbus,
OH (US); Thomas Roukis, Winter
Garden, FL (US)

(*) Notice: Subject to any disclaimer, the term of this
patent is extended or adjusted under 35
U.S.C. 154(b) by 0 days.

(21) Appl. No.: 19/015,265

(22) Filed: Jan. 9, 2025

(51) Int. Cl.
*A61F 2/46* (2006.01)
*A61F 2/30* (2006.01)

(52) U.S. Cl.
CPC .. *A61F 2/4675* (2013.01); *A61F 2002/30003*
(2013.01)

(58) Field of Classification Search
CPC ...................................................... A61F 2/4675
See application file for complete search history.

(56) References Cited

U.S. PATENT DOCUMENTS

| | | | |
|---|---|---|---|
| 6,758,849 B1 * | 7/2004 | Michelson | .......... A61F 2/30744 606/247 |
| 7,070,621 B2 * | 7/2006 | Castro | ................... A61F 2/4611 623/17.11 |
| 2003/0023307 A1 * | 1/2003 | Michelson | .............. A61F 2/446 623/17.11 |
| 2004/0153160 A1 * | 8/2004 | Carrasco | ............... A61F 2/4611 623/17.15 |
| 2016/0250026 A1 * | 9/2016 | Dee | ....................... A61F 2/2846 623/20.16 |

* cited by examiner

*Primary Examiner* — Tessa M Matthews
(74) *Attorney, Agent, or Firm* — Brennan, Manna &
Diamond, LLC

(57) ABSTRACT

A subchondral implant is disclosed, which is designed as a
bone void filler for damaged bone tissue. The subchondral
implant comprises a body component configured in a cylin-
drical shape with a hollow interior cavity and an exterior
curved sidewall. The curved sidewall includes a plurality of
helical ribs in a spaced apart manner for optimal fixation.
The top surface comprises a plurality of through-holes for
sutures, when securing tissue graft. An adjacent subchondral
implant can be utilized with the subchondral implant and is
nested against it for use. The nested implants allow users to
repair large, elongated areas that may not be repaired by a
single subchondral implant.

1 Claim, 4 Drawing Sheets

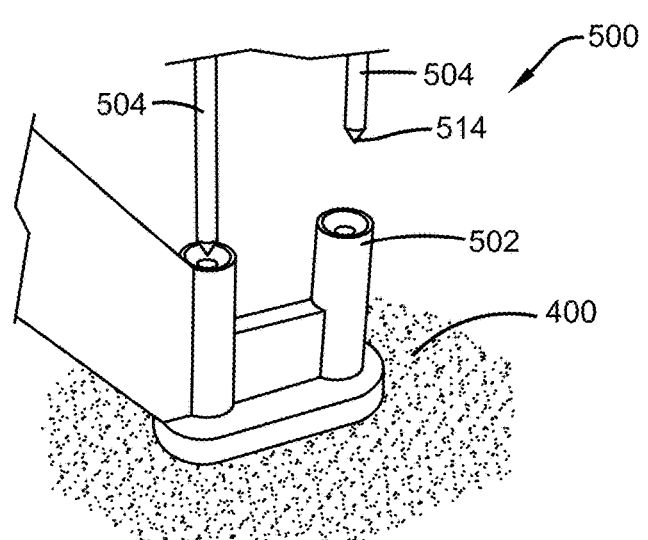
FIG. 5A
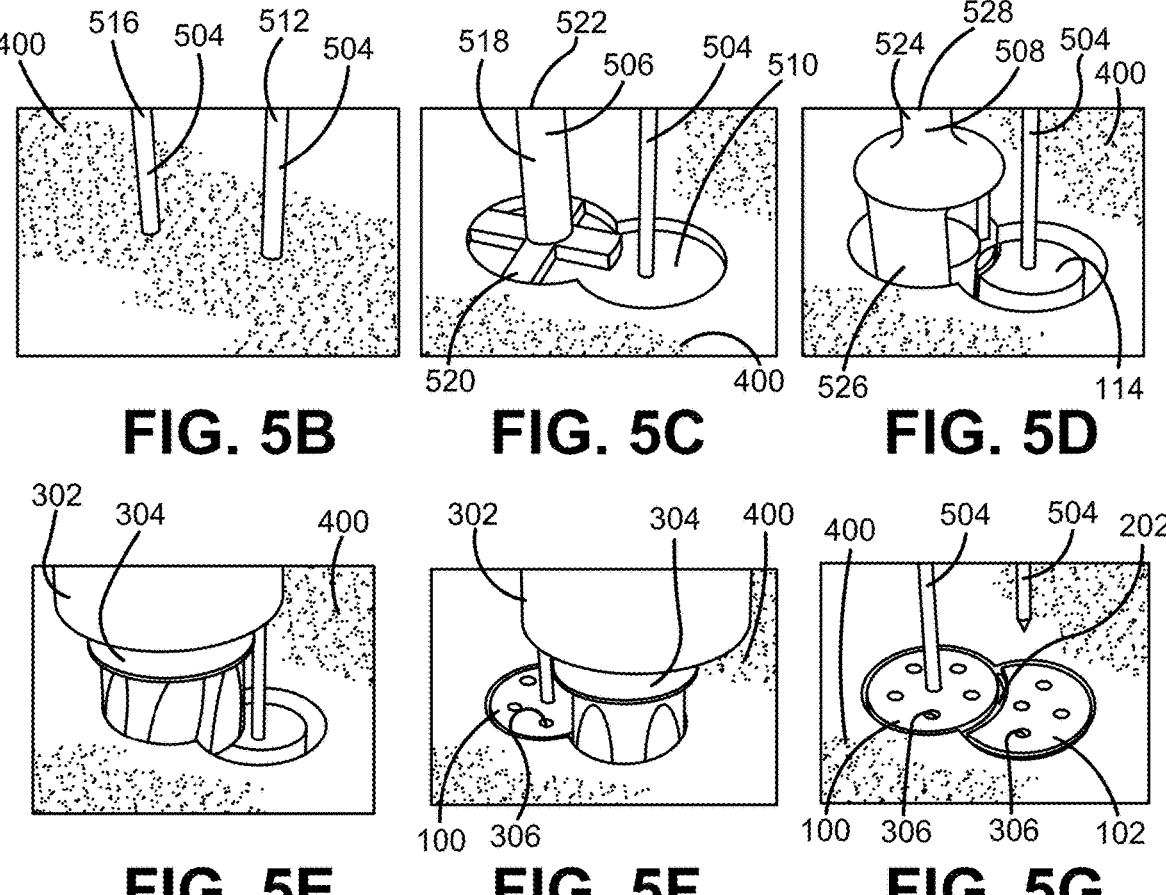
FIG. 5B  FIG. 5C  FIG. 5D
FIG. 5E  FIG. 5F  FIG. 5G

SUBCHONDRAL IMPLANT SYSTEM

FIELD OF THE INVENTION

The present invention relates generally to a medical device for use in the field of podiatry. More particularly, the present invention relates to a subchondral implant system that may be used as a bone void filler to provide a ridged structure for damaged bone tissue. This implant system allows the surgeon to expand the area of repair by using an adjacent nested implant when needed. Accordingly, the present disclosure makes specific reference thereto. Nonetheless, it is to be appreciated that aspects of the present invention are also equally applicable to other like applications, devices and methods of manufacture.

BACKGROUND

By way of background, articular cartilage is a smooth, white tissue which covers the ends of bones where they come together to form joints in humans and many animals so as to facilitate articulation of the joints and protect and cushion the bones. Subchondral bone is the bone that is underneath the cartilage and provides support to the cartilage. Cartilage or subchondral bone may become damaged, however, due to disease, abrupt trauma, prolonged wear or other factors. A number of surgical techniques have been developed to treat damaged osteochondral and subchondral defects. Treating osteochondral/subchondral defects is known to relieve pain and facilitate better joint function, as well as potentially delaying or preventing the onset of arthritis.

Furthermore, there are a variety of conditions and diseases that impair the integrity and function of human joints. Among these joint conditions and diseases are arthroses, chondromalacia patella, isolated chondral defect, juvenile idiopathic arthritis, ligamentous deficiency arthroses, osteoarthritis (degenerative arthritis or degenerative joint disease), osteonecrosis, osteochondritis dissecans, patellar instability, post-ligamentous injury arthritis, post-meniscectomy arthritis, post-meniscectomy arthroses, post-traumatic arthritis, rheumatoid arthritis and septic arthritis. Treatment of joint conditions and diseases includes surgery and the administration of therapeutic agents. However, none of these treatments ameliorate all of the joint conditions and diseases.

Accordingly, it would be desirable to provide an implant that acts as a bone void filler to provide a ridged structure for damaged bone tissue. Further, it would be desirable to allow the surgeon to expand the area of repair by using an adjacent nested implant when needing to repair large, elongated areas that may not be repaired by a single implant.

The subject matter disclosed and claimed herein, in one embodiment thereof, comprises a subchondral implant system. The subchondral implant system is designed as a bone void filler for damaged bone tissue. The subchondral implant system comprises a body component configured in a cylindrical shape. The body component comprises a top surface, a bottom opening, and a curved sidewall. The bottom opening allows for access to the hollow interior cavity of the body component. The curved sidewall includes a plurality of helical ribs in a spaced apart manner for optimal fixation. The top surface comprises a plurality of through-holes for sutures, when securing tissue graft.

In another embodiment, an adjacent subchondral implant can be utilized with the subchondral implant. The adjacent subchondral implant comprises a body component with a curved, cutaway from the top surface to the bottom opening, creating a nesting feature. Specifically, the curved, cutaway allows the adjacent subchondral implant to be nested against the subchondral implant, which allows users to repair large, elongated areas that may not be repaired by a single subchondral implant.

In use, a k-wire is inserted in the bone tissue in the intended location. A canulated counter-boring reamer is used to create a blind hole or holes, depending on if just the subchondral implant is being inserted or the subchondral implant and the adjacent subchondral implant are being inserted. Then, a canulated coring reamer is used to create a cylindrical core which will be used to fixate the implant. Then, the subchondral implant is installed using an inserter instrument and a mallet. Finally, an adjacent subchondral implant is inserted if needed and the k-wires are removed.

In this manner, the subchondral implant of the present invention accomplishes all of the forgoing objectives and provides users with an implant that fills a bone void for damaged bone tissue. The subchondral implant can be a full cylindrical implant or is used with an adjacent subchondral implant that is made to nest beside the full subchondral implant to repair large, elongated areas that cannot be repaired by a single subchondral implant.

SUMMARY OF THE INVENTION

The following presents a simplified summary in order to provide a basic understanding of some aspects of the disclosed innovation. This summary is not an extensive overview, and it is not intended to identify key or critical elements or to delineate the scope thereof. Its sole purpose is to present some concepts in a simplified form as a prelude to the more detailed description that is presented later.

The subject matter disclosed and claimed herein, in one embodiment thereof, comprises a subchondral implant. The subchondral implant is designed as a bone void filler for damaged bone tissue. The subchondral implant comprises a body component configured in a cylindrical shape with a hollow interior cavity and curved sidewall. The curved sidewall includes a plurality of helical ribs in a spaced apart manner for optimal fixation. The top surface comprises a plurality of through-holes for sutures, when securing tissue graft. In another embodiment, an adjacent subchondral implant can be nested with the subchondral implant.

In one embodiment, the subchondral implant comprises a body component configured in a cylindrical shape. The body component comprises a top surface and a bottom opening that share a curved cylindrical sidewall extending therebetween. The bottom opening allows for access to the hollow interior cavity of the body component. The hollow interior cavity is a cylindrical inner core for accepting a center core of bone during insertion.

In one embodiment, the implant is configured to be press-fit into an osteochondral hole bored at a patient's defect area. The top surface includes a shape that approximates an osteochondral surface to be replaced. The bottom opening is configured to be implanted into the osteochondral hole drilled into the patient's bone. The implant may comprise any synthetic or natural homogenous material suitable for implantation into bone, including any one or more of collagen, human or animal allograft, silicone, bio glass, collagen, PEEK, polyethylene, titanium, cobalt chrome, and the like, but is typically manufactured of PEEK.

In one embodiment, the subchondral implant may be implemented with a range of diameters that facilitate using the implant to treat osteochondral or subchondral defects in various bone joint locations in the human body, such as by way of non-limiting example, a femoral condyle, a humeral head, a talus, the trapezium of the hand, the capitellum of the elbow, as well as any of the metatarsal and phalangeal joints of the hand or foot. It is contemplated, however, that the overall size of the implant is to be selected according to the particular bone joint to be treated.

In one embodiment, the implant possesses a height along a longitudinal axis of the implant and a bottom diameter centered on the longitudinal axis. The height extends from the bottom opening to the highest region of the top surface, such as the region of the top surface around the longitudinal axis. In one embodiment, the height is substantially 4-10 millimeters (mm). It is contemplated, however, that the height may be varied according to the bone joint to be treated, and therefore the implant may be implemented with a wide variety of heights, without limitation.

In one embodiment, the diameter of the top surface is substantially the same as the bottom diameter of the bottom opening, and thus the cylindrical sidewall comprises a straight cylindrical shape, without limitation. In one embodiment, the diameter is substantially 4-10 millimeters (mm). It is contemplated, however, that the diameter may be varied according to the bone joint to be treated, and therefore the implant may be implemented with a wide variety of diameters, without limitation. In such embodiments, a practitioner may select the implant based on a size of the osteochondral hole to be drilled into the patient's bone.

In one embodiment, when the subchondral implant is implanted into an osteochondral hole, the top surface of the implant is disposed flush or slightly below the surrounding cartilage tissue of the bone. In general, the top surface includes a shape configured to approximate the osteochondral surface to be replaced. In some embodiments, the shape of the top surface includes a convex curvature that approximates the curvature of the osteochondral surface to be replaced. For subchondral implants, the top surface may have a flat curvature as the implant generally is disposed below the surrounding articular surface and therefore does not need to approximate the shape of articular surface.

In one embodiment, the bottom opening allows for access to the hollow interior cavity of the body component. Specifically, when reaming the hole in the bone, the reamer only cuts the outside and leaves a center core of bone. Further, the hollow interior cavity encompasses this center core, such that the bottom opening is in contact with a bottom of the center core of bone to elevate the top surface flush or slightly below the surrounding cartilage tissue of the bone. The center core of bone positioned within the hollow interior cavity advantageously prevents subsidence of the implant into the osteochondral hole, even in the event that the bone below the bottom opening subsides. Furthermore, the subchondral implant is typically manufactured of PEEK, which prevents the implant from subsiding.

In one embodiment, the cylindrical sidewall comprises a plurality of helical ribs for optimal fixation. The helical ribs protrude into the surrounding bone when the implant is inserted. Typically, the ribs protrude approximately ¼-½ mm radially. Any suitable number of ribs can be utilized as is known in the art. Further, the ribs are configured in a spaced apart manner. Typically, the helical ribs are spaced apart, such that they have a pitch of approximately 2-3 millimeters to promote boney apposition. Upon insertion, the subchondral implant is positioned axially over the center core of bone and persuaded into place via a mallet and insertion tamp. This makes it possible to manufacture the implant out of a radiolucent polymer, such as PEEK, which performs well in compression, especially when being persuaded into place via the mallet. Further, prior technology uses threads as the fixation method, which requires the use of a non-radiolucent metal. The use of PEEK does not do well with a torsional load, as such a user would not want to twist or torque the implant into the hole, as in the prior technology. The PEEK material is radiolucent, which will allow for better post-surgery monitoring using x-ray imaging. Also, PEEK is more workable by drilling or cutting with various surgical instruments.

In one embodiment, the top surface comprises a plurality of through-holes for sutures, when securing tissue graft. Any suitable number of through-holes can be utilized as is known in the art. Further, the through-holes can be any suitable shape and size as is known in the art, depending on the user's wants and/or needs.

In one embodiment, an adjacent subchondral implant can be utilized with the subchondral implant. The adjacent subchondral implant comprises a body component with a curved, cutaway from the top surface to the bottom opening, creating a nesting feature. The adjacent subchondral implant comprises the same body structures as the subchondral implant with the addition of the nesting feature. The nesting feature is typically a semi-circle, such that it can contact and nest against the cylindrical subchondral implant. Specifically, the curved, cutaway allows the adjacent subchondral implant to be nested against the subchondral implant, creating a larger surface area for the pair of implants, which allows users to repair oblong, elongated, or larger areas that may not be repaired by a single subchondral implant.

In one embodiment, multiple adjacent subchondral implants and subchondral implants are utilized to repair a large area. For example, multiple adjacent subchondral implants can be nested against one subchondral implant. In another example, the multiple adjacent subchondral implants can be daisy-chained together from one subchondral implant. Any suitable number of adjacent subchondral implants and subchondral implants can be utilized together, depending on the shape and size of the area to be repaired and other anatomical conditions.

In one embodiment, the subchondral implant system for treating osteochondral/subchondral defects according to the present disclosure includes one or more subchondral implants, one or more adjacent subchondral implants, a positioning jig, a k-wire, a cannulated counter-boring reamer, a cannulated coring reamer, a mallet, and insertion tamp. As will be appreciated, the subchondral implant system comprises instruments necessary for treating osteochondral/subchondral defects by way of surgery. The sizes of the instruments comprising the implant system will depend upon the size of the particular implant to be implanted into the patient. It is envisioned, therefore, that a surgeon may select the implant and a correspondingly sized instrument based on the location and size of the bone joint to be treated. The instruments comprising the subchondral implant system are not to be limited to the specific instruments, or the sizes and shapes of the instruments disclosed.

In operation, first, a positioning jig is placed on the desired location and a k-wire (i.e., 1 mm k-wire) is inserted in the bone tissue in the intended location of the subchondral implant and the adjacent subchondral implant, if an adjacent subchondral implant is being inserted. Next, a cannulated counter-boring reamer is used with each k-wire to create two overlapping blind holes. Then, a cannulated coring reamer is used to create two cylindrical cores (i.e., center core of bone) which will be used to fixate the implants. Then, the subchondral implant is installed using the insertion tamp and a mallet. Next, the adjacent subchondral implant is installed using the insertion tamp and a mallet. Finally, both k-wires are removed.

In one embodiment, the positioning jig is a conventional jig for positioning at least one k-wire. Any suitable positioning jig can be utilized as is known in the art to position one or more k-wires at one time. The k-wire comprises an elongated shaft having a distal pointed tip and a proximal blunt end. The k-wire is typically 1 mm in size and is configured to be inserted into confined spaces within bone joints and serves to direct a subsequent insertion of the cannulated counter-boring reamer to the implant location within the bone joint. It will be appreciated that the distal pointed tip facilitates advancing the k-wire through obstructive tissues and structures, and the proximal blunt end facilitates manipulating the k-wire by hand, or by way of an appropriate tool.

In one embodiment, the cannulated counter-boring reamer comprises rigid elongate shaft having a distal cutting end and a proximal shank. The distal cutting end comprises a cutting edge suitable for rotatably clearing an osteochondral bore, thereby removing damaged articular cartilage and an underlying bone portion from the bone joint being treated. The proximal shank is configured to be grasped by a chuck of a surgical drill, or other equivalent rotary tool. Further, in some embodiments the cannulated counter-boring reamer comprises a central, lengthwise hole whereby the reamer may be mounted onto the k-wire so as to direct the distal cutting end to the damage location within the bone joint.

In one embodiment, the cannulated coring reamer comprises a rigid elongate shaft having a distal cutting end and a proximal shank. The distal cutting end comprises two or more curved, elongated cutting blades, which spin during use to cut a cylindrical core. Specifically, the distal cutting end is suitable for creating center cores of bone for the implant to be positioned on top of, during insertion. The proximal shank is configured to be grasped by a chuck of a surgical drill, or other equivalent rotary tool. Further, in some embodiments the cannulated coring reamer comprises a central, lengthwise hole whereby the reamer may be mounted onto the k-wire so as to direct the distal cutting end to the damage location within the bone joint.

In one embodiment, the mallet is a flat-ended hammer, which is used with the insertion tamp to drive the subchondral implant and/or adjacent subchondral implant into the bone, around the center core created by the coring reamer. Once inserted, the implants are flush with or sub-flush to the cortical surface of the bone or the cartilage of the bone.

In general, it is contemplated that the subchondral implant system is to be suitably sterilized for surgeries and packaged into sterilized containers.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which:

FIGS. 5A-5G illustrate a perspective view of the procedure for inserting the subchondral implant and adjacent subchondral implant of the present invention in accordance with the disclosed architecture.

DETAILED DESCRIPTION

Figures 1A, 1B, 1C, 2A, 2B, 2C:
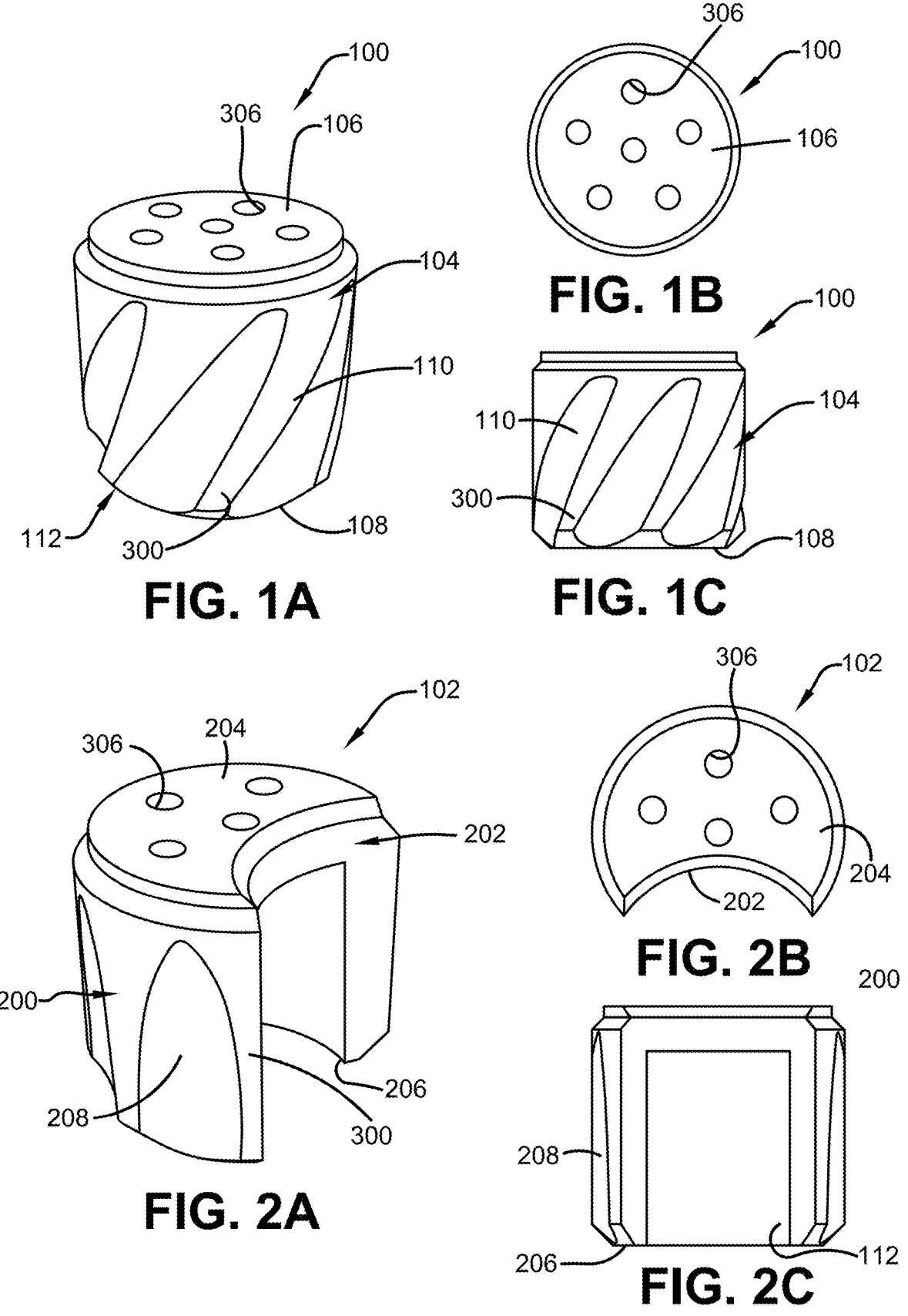
FIGS. 1A-1C illustrate a perspective view of the subchondral implant of the present invention in accordance with the disclosed architecture.
FIGS. 2A-2C illustrate a perspective view of the adjacent subchondral implant of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

In this application, the words proximal, distal, anterior or plantar, posterior or dorsal, medial and lateral are defined by their standard usage for indicating a particular part or portion of a bone, or directional terms of reference, according to the relative disposition of the natural bone. For example, "proximal" means the portion of a bone nearest the torso, while "distal" indicates the portion of the bone farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regard to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the foot for brevity purposes, but it should be understood that the devices, instrumentation, and methods may be used with other bones of the body having similar structures, for example the upper extremity, and more specifically, with the bones of the wrist, hand, and arm.

As noted above, there is a long felt need in the art for devices, instrumentation, and methods of inserting the subchondral implant and possible adjacent subchondral implant. Specifically, devices, instrumentation and methods used to fill a bone void for damaged bone tissue.

The present invention, in one exemplary embodiment, is a novel subchondral implant system. The system comprises a subchondral implant which fills a bone void for damaged bone tissue. The subchondral implant comprises a cylindrical structure with helical ribs and multiple suture holes. The instrumentation includes at least a k-wire, a cannulated counter-boring reamer, a cannulated coring reamer, a mallet, and an insertion tamper, among other instruments.

Referring initially to the drawings, FIGS. 1-5 illustrate multiple views of the subchondral implant 100 and the adjacent subchondral implant 102 of the present invention. In the present embodiment, the subchondral implant 100 is an improved subchondral implant 100 that fills a bone void for damaged bone tissue 400. The implant 100 and 102 is especially designed to allow any doctor, surgeon, etc., or any other suitable user as is known in the art, to fill a bone void, or other larger, elongated area dependent on anatomical conditions. More specifically, the subchondral implant system 500 comprises the subchondral implant 100, the adjacent subchondral implant 102, and instrumentation for inserting the subchondral implant 100 and adjacent subchondral implant 102.

As shown in FIGS. 1A-C, the subchondral implant 100 comprises a body component 104 configured in a cylindrical shape. The body component 104 comprises a top surface 106 and a bottom opening 108 that share a curved cylindrical sidewall 110 extending therebetween. The bottom opening 108 allows for access to the hollow interior cavity 112 of the body component 104. The hollow interior cavity 112 is a cylindrical inner core for accepting a center core of bone 114 during insertion.

Further, the implant 100 is configured to be press-fit into an osteochondral hole (not shown) bored at a patient's defect area. The top surface 106 includes a shape that approximates an osteochondral surface to be replaced. The bottom opening 108 is configured to be implanted into the osteochondral hole drilled into the patient's bone. The implant 100 may comprise any synthetic or natural homogenous material suitable for implantation into bone, including any one or more of collagen, human or animal allograft, silicone, bio glass, collagen, PEEK, polyethylene, titanium, cobalt chrome, and the like, but is typically manufactured of PEEK.

Additionally, the subchondral implant 100 may be implemented with a range of diameters that facilitate using the implant 100 to treat osteochondral or subchondral defects in various bone joint locations in the human body, such as by way of non-limiting example, a femoral condyle, a humeral head, a talus, the trapezium of the hand, the capitellum of the elbow, as well as any of the metatarsal and phalangeal joints of the hand or foot. It is contemplated, however, that the overall size of the implant 100 is to be selected according to the particular bone joint to be treated.

Furthermore, the implant 100 possesses a height along a longitudinal axis of the implant 100 and a bottom diameter centered on the longitudinal axis. The height extends from the bottom opening 108 to the highest region of the top surface 106, such as the region of the top surface 106 around the longitudinal axis. In one embodiment, the height is substantially 4-10 millimeters (mm). It is contemplated, however, that the height may be varied according to the bone joint to be treated, and thus the implant 100 may be implemented with a wide variety of heights, without limitation.

Additionally, the diameter of the top surface 106 is substantially the same as the bottom diameter of the bottom opening 108, and thus the cylindrical sidewall 110 comprises a straight cylindrical shape, without limitation. In one embodiment, the diameter is substantially 4-10 millimeters (mm). It is contemplated, however, that the diameter may be varied according to the bone joint to be treated, and thus the implant 100 may be implemented with a wide variety of diameters, without limitation. In such embodiments, a practitioner may select the implant 100 based on a size of the osteochondral hole to be drilled into the patient's bone.

Further, when the subchondral implant 100 is implanted into an osteochondral hole, the top surface 106 of the implant 100 is disposed flush or slightly below the surrounding cartilage tissue of the bone. In general, the top surface 106 includes a shape configured to approximate the osteochondral surface to be replaced. In some embodiments, the shape of the top surface 106 includes a convex curvature that approximates the curvature of the osteochondral surface to be replaced. For subchondral implants 100, the top surface 106 may have a flat curvature as the implant 100 generally is disposed below the surrounding articular surface and thus does not need to approximate the shape of articular surface.

Additionally, the bottom opening 108 allows for access to the hollow interior cavity 112 of the body component 104. Specifically, when reaming the hole in the bone, the reamer only cuts the outside and leaves a center core of bone 114. Further, the hollow interior cavity 112 encompasses this center core 114, such that the bottom opening 108 is in contact with a bottom of the center core of bone 114 to elevate the top surface 106 flush or slightly below the surrounding cartilage tissue of the bone. The center core of bone 114 positioned within the hollow interior cavity 112 advantageously prevents subsidence of the implant 100 into the osteochondral hole, even in the event that the bone below the bottom opening 108 subsides. Furthermore, the subchondral implant 100 is typically manufactured of PEEK, which prevents the implant 100 from subsiding, due to the characteristics of the PEEK material.

As shown in FIGS. 2A-C, an adjacent subchondral implant 102 can be utilized with the subchondral implant 100. The adjacent subchondral implant 102 comprises a body component 200 with a curved, cutaway (i.e., nesting feature 202) from the top surface 204 to the bottom opening 206, creating a nesting feature 202. The adjacent subchondral implant 102 comprises the same body structures (i.e., top surface 204, bottom opening 206, curved sidewall 208) as the subchondral implant 100 with the addition of the nesting feature 202. The nesting feature 202 is typically a semi-circle, such that it can contact and nest against the cylindrical subchondral implant 100. Specifically, the curved, cutaway (i.e., nesting feature 202) allows the adjacent subchondral implant 102 to be nested against the subchondral implant 100, creating a larger surface area for the pair of implants 100, 102, which allows users to repair oblong, elongated, or larger areas that may not be repaired by a single subchondral implant 100.

Figure 3A:
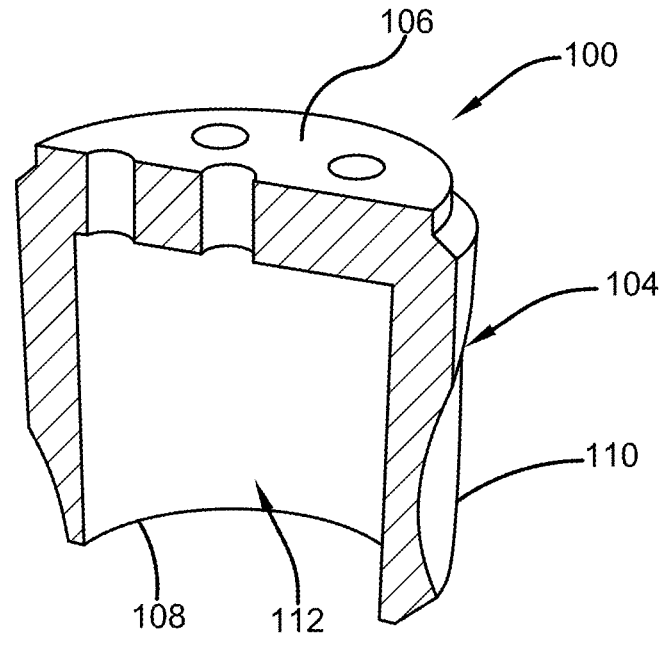
FIGS. 3A-3B illustrate a perspective view of the subchondral implant of the present invention showing the suture holes and helical ribs of the implant in accordance with the disclosed architecture.
Figure 3B:
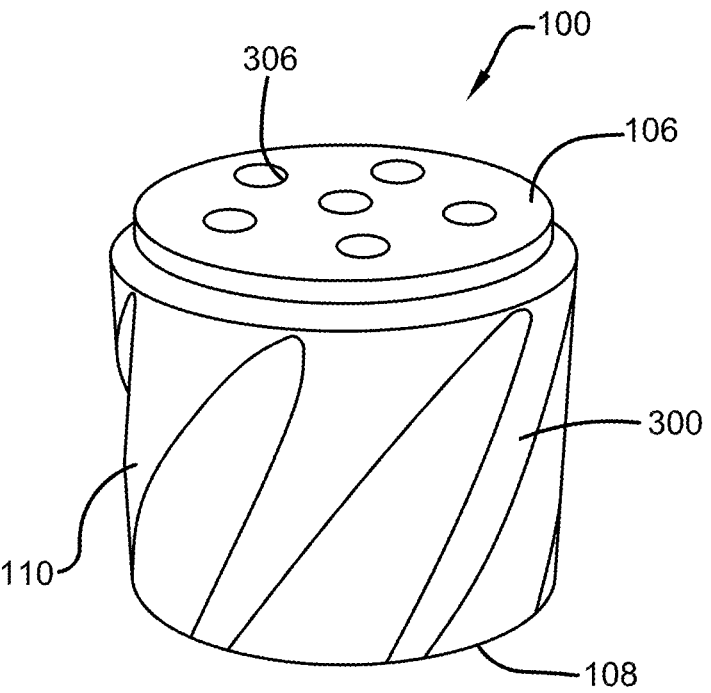

As shown in FIGS. 3A-B, the cylindrical sidewall 110 and 208 comprises a plurality of helical ribs 300 for optimal fixation. The helical ribs 300 protrude into the surrounding bone when the implant 100, 102 is inserted. Typically, the ribs 300 protrude approximately ¼-½ mm radially. Any suitable number of ribs 300 can be utilized as is known in the art. Further, the ribs 300 are configured in a spaced apart manner. Typically, the helical ribs 300 are spaced apart, such that they have a pitch of approximately 2-3 millimeters to promote boney apposition. Upon insertion, the subchondral implant 100 (and adjacent subchondral implant 102) is positioned axially over the center core of bone 114 and persuaded into place via a mallet 302 and insertion tamp 304 (shown in FIG. 5). This makes it possible to manufacture the implant 100, 102 out of a radiolucent polymer, such as PEEK, which performs well in compression, especially when being persuaded into place via the mallet 302. Further, prior technology uses threads as the fixation method, which requires the use of a non-radiolucent metal. The use of PEEK does not do well with a torsional load, as such a user would not want to twist or torque the implant 100, 102 into the hole, as in the prior technology. The PEEK material is radiolucent, which will allow for better post-surgery monitoring using x-ray imaging. Also, PEEK is more workable by drilling or cutting with various surgical instruments.

Furthermore, the top surface 106, 204 comprises a plurality of through-holes 306 for sutures (not shown), when securing tissue graft. Any suitable number of through-holes 306 can be utilized as is known in the art. Further, the through-holes 306 can be any suitable shape and size as is known in the art, depending on the user's wants and/or needs.

Figures 4A, 4B:
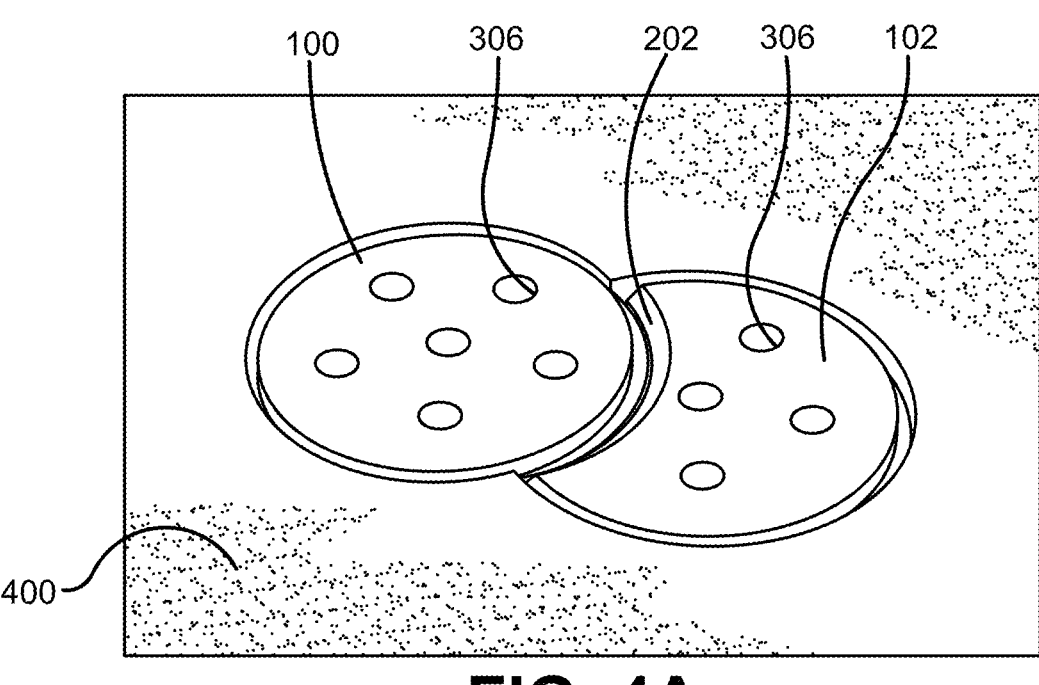
FIGS. 4A-4B illustrate a perspective view of the subchondral implant and adjacent subchondral implant of the present invention nested together in accordance with the disclosed architecture.

As shown in FIGS. 4A-B, multiple adjacent subchondral implants 102 and subchondral implants 100 are utilized to repair a large area. For example, multiple adjacent subchondral implants 102 can be nested against one subchondral implant 100. In another example, the multiple adjacent subchondral implants 102 can be daisy-chained together and extend from one subchondral implant 100. Thus, any suitable number of adjacent subchondral implants 102 and subchondral implants 100 can be utilized together, depending on the shape and size of the area to be repaired and other anatomical conditions.

As shown in FIGS. 5A-G, the subchondral implant system 500 for treating osteochondral/subchondral defects according to the present disclosure includes one or more subchondral implants 100, one or more adjacent subchondral implants 102, a positioning jig 502, a k-wire 504, a cannulated counter-boring reamer 506, a cannulated coring reamer 508, a mallet 302, and insertion tamp 304. As will be appreciated, the subchondral implant system 500 comprises instruments 502, 504, 506, 508, 302, 304 necessary for treating osteochondral/subchondral defects by way of surgery. The sizes of the instruments 502, 504, 506, 508, 302, 304 comprising the implant system 500 will depend upon the size of the particular implant 100, 102 to be implanted into the patient. It is envisioned, therefore, that a surgeon may select the implant 100, 102 and a correspondingly sized instrument based on the location and size of the bone joint to be treated. The instruments 502, 504, 506, 508, 302, 304 comprising the subchondral implant system 500 are not to be limited to the specific instruments, or the sizes and shapes of the instruments disclosed.

A surgical method for filling a bone void for damaged bone tissue 400, will now be described. The method utilizes some of the devices, instruments, features, aspects, components and the like described above, and therefore reference will be made to the above-described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

In operation, first, a positioning jig 502 is placed on the desired location and a k-wire 504 (i.e., 1 mm k-wire 504) is inserted in the bone tissue 400 in the intended location of the subchondral implant 100 and the adjacent subchondral implant 102, if an adjacent subchondral implant 102 is being inserted. Next, a cannulated counter-boring reamer 506 is used with each k-wire 504 to create two overlapping blind holes 510. Then, a cannulated coring reamer 508 is used to create two cylindrical cores (i.e., center core of bone 114) which will be used to fixate the implants 100, 102. Then, the subchondral implant 100 is installed using the insertion tamp 304 and a mallet 302. Next, the adjacent subchondral implant 102 is installed using the insertion tamp 304 and a mallet 302. Finally, both k-wires 504 are removed and the patient is closed.

Generally, the positioning jig 502 is a conventional jig for positioning at least one k-wire 504. Any suitable positioning jig 502 can be utilized as is known in the art to position one or more k-wires 504 at one time. The k-wire 504 comprises an elongated shaft 512 having a distal pointed tip 514 and a proximal blunt end 516. The k-wire 504 is typically 1 mm in size and is configured to be inserted into confined spaces within bone joints and serves to direct a subsequent insertion of the cannulated counter-boring reamer 506 to the implant 100, 102 location within the bone joint. It will be appreciated that the distal pointed tip 514 facilitates advancing the k-wire 504 through obstructive tissues and structures, and the proximal blunt end 516 facilitates manipulating the k-wire 504 by hand, or by way of an appropriate tool.

Further, the cannulated counter-boring reamer 506 comprises a rigid elongate shaft 518 having a distal cutting end 520 and a proximal shank 522. The distal cutting end 520 comprises a cutting edge suitable for rotatably clearing an osteochondral bore, thereby removing damaged articular cartilage and an underlying bone portion from the bone joint being treated. The proximal shank 522 is configured to be grasped by a chuck of a surgical drill, or other equivalent rotary tool (not shown). Further, in some embodiments the cannulated counter-boring reamer 506 comprises a central, lengthwise hole (not shown) whereby the reamer 506 may be mounted onto the k-wire 504 so as to direct the distal cutting end 520 to the damage location within the bone joint.

Additionally, the cannulated coring reamer 508 comprises a rigid elongate shaft 524 having a distal cutting end 526 and a proximal shank 528. The distal cutting end 526 comprises two or more curved, elongated cutting blades, which spin during use to cut a cylindrical core 114. Specifically, the distal cutting end 526 is suitable for creating center cores of bone 114 for the implant 100, 102 to be positioned on top of, during insertion. The proximal shank 528 is configured to be grasped by a chuck of a surgical drill, or other equivalent rotary tool (not shown). Further, in some embodiments the cannulated coring reamer 508 comprises a central, lengthwise hole (not shown) whereby the reamer 508 may be mounted onto the k-wire 504 so as to direct the distal cutting end 526 to the damage location within the bone joint.

Furthermore, the mallet 302 is a flat-ended hammer, which is used with the insertion tamp 304 to drive the subchondral implant 100 and/or adjacent subchondral implant 102 into the bone, around the center core 114 created by the coring reamer 508. Once inserted, the implants 100, 102 are flush with or sub-flush to the cortical surface of the bone or the cartilage of the bone, as desired.

In general, it is contemplated that the subchondral implant system 500 is to be suitably sterilized for surgeries and packaged into sterilized containers (not shown).

Certain terms are used throughout the following description and claims to refer to particular features or components. As one skilled in the art will appreciate, different users may refer to the same feature or component by different names. This document does not intend to distinguish between components or features that differ in name but not structure or function. As used herein "subchondral implant" and "implant" are interchangeable and refer to the subchondral implant 100 of the present invention.

Notwithstanding the forgoing, the subchondral implant 100 of the present invention can be of any suitable size and configuration as is known in the art without affecting the overall concept of the invention, provided that it accomplishes the above stated objectives. One of ordinary skill in the art will appreciate that the subchondral implant 100 as shown in FIGS. 1-5 is for illustrative purposes only, and that many other sizes and shapes of the subchondral implant 100 are well within the scope of the present disclosure. Although the dimensions of the subchondral implant 100 are important design parameters for user convenience, the subchondral implant 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A surgical method for filling a bone void for damaged bone tissue, the surgical method comprising the following steps:

placing a positioning jig on a desired location to be repaired;

inserting a k-wire through the positioning jig and into bone tissue in an intended location of a subchondral implant and an adjacent subchondral implant to be inserted;

utilizing a cannulated counter-boring reamer to create two overlapping blind holes;

utilizing a cannulated coring reamer to create two center cores of bone, used to fixate the subchondral implant and the adjacent subchondral implant;

installing the subchondral implant using an insertion tamp and a mallet;

installing the adjacent subchondral implant using the insertion tamp and the mallet; and removing the k-wire and closing the patient.

\* \* \* \* \*